US006391023B1

United States Patent
Weber et al.

(12) United States Patent
(10) Patent No.: US 6,391,023 B1
(45) Date of Patent: *May 21, 2002

(54) THERMAL RADIATION FACELIFT DEVICE

(75) Inventors: Paul J. Weber, Ft. Lauderdale, FL (US); Luiz B. Da Silva, Danville; Alexander M. Rubenchik, Livermore, both of CA (US)

(73) Assignee: Pearl Technology Holdings, LLC, Clearwater, FL (US)

( * ) Notice: Subject to any disclaimer, the term of this patent is extended or adjusted under 35 U.S.C. 154(b) by 22 days.

This patent is subject to a terminal disclaimer.

(21) Appl. No.: 09/588,436

(22) Filed: Jun. 6, 2000

Related U.S. Application Data

(63) Continuation-in-part of application No. 09/085,948, filed on May 28, 1998, now Pat. No. 6,203,540.
(51) Int. Cl.[7] .............................................. A61B 18/18
(52) U.S. Cl. .................... 606/15; 606/2; 606/9
(58) Field of Search .................. 606/2, 3, 7, 10–17, 606/32, 41, 50

(56) References Cited

U.S. PATENT DOCUMENTS

| | | | |
|---|---|---|---|
| 4,582,057 A | * | 4/1986 | Auth et al. ............... 128/303.1 |
| 5,695,510 A | | 12/1997 | Hood |
| 5,827,267 A | * | 10/1998 | Savage et al. ................ 606/16 |
| 5,871,524 A | | 2/1999 | Knowlton |
| 5,935,143 A | | 8/1999 | Hood |
| 5,948,011 A | | 9/1999 | Knowlton |
| 5,984,915 A | | 11/1999 | Loeb et al. |
| 6,033,398 A | * | 3/2000 | Farley et al. .................. 606/27 |
| 6,176,854 B1 | | 1/2001 | Cone |
| 6,176,857 B1 | * | 1/2001 | Ashley .......................... 606/32 |
| 6,203,540 B1 | * | 3/2001 | Weber ........................... 606/15 |
| 6,241,753 B1 | | 6/2001 | Knowlton |
| 6,264,652 B1 | | 7/2001 | Eggers et al. |
| 6,277,116 B1 | | 8/2001 | Utely et al. |

OTHER PUBLICATIONS

P.J. Weber et al., Bulbous–Lysing Underminers, J. Dermatol Surg. Oncol., 15:12, Dec. 1989, pp. 1252–1253.

* cited by examiner

*Primary Examiner*—Michael Peffley
*Assistant Examiner*—Pete J Vrettakos
(74) *Attorney, Agent, or Firm*—John P. Wooldridge

(57) ABSTRACT

A device is described that can be used by surgeons to provide quick and accurate face-lifting maneuvers that minimize the amount of tissue that has to be removed. The device comprised of a hollow undermining shaft with specially designed tip that can safely separate tissue planes and lyse fibrous tissue. Thermal radiation can be delivered down the shaft to heat and cause tissue contraction. The device can also include a temperature sensor that can be used to control the thermal radiation. Optionally, the device can also use ultrasound or electro surgical energy to improve tissue lysing.

32 Claims, 3 Drawing Sheets

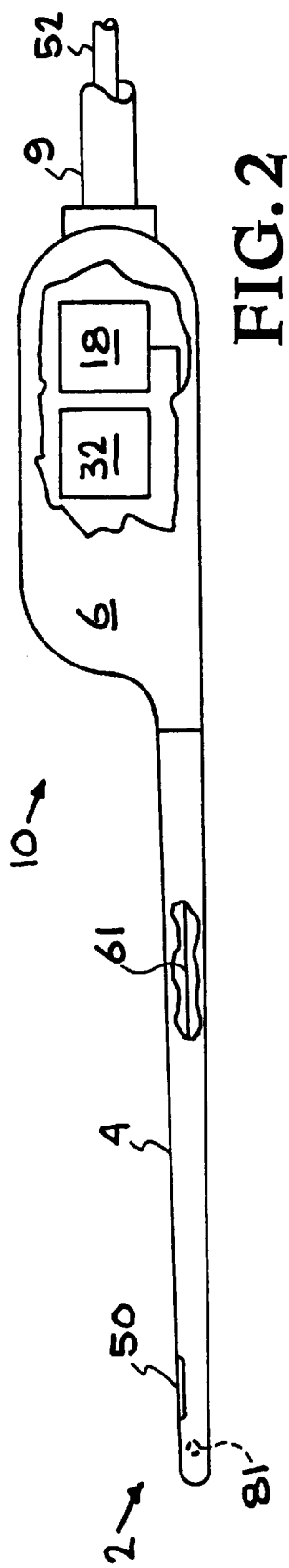
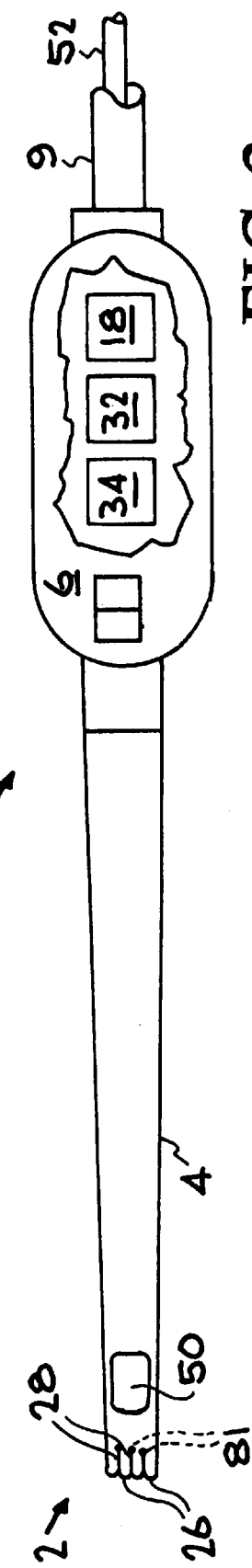
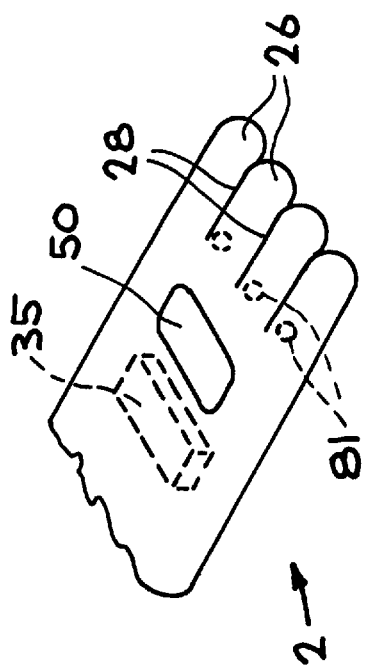

THERMAL RADIATION FACELIFT DEVICE

This application is a continuation-in-part of U.S. patent application Ser. No. 09/085,948, now U.S. Pat. No. 6,203, 540 filed May 28, 1998, incorporated herein by reference.

BACKGROUND OF THE INVENTION

1. Field of the Invention

This invention relates to a surgical device for performing face-lifting using thermal radiation, and more specifically to a face-lifting device with a specialized tip design that delivers heat The invention provides a surgical device that can improve the accuracy and speed of face-lift operations. Use of the present invention controllably causes thermally related healing contraction of the target tissues thus allowing face lifting in younger patients without the removal or cutting-out of skin in properly selected patients. The use of the present invention may also aid in the performance and results of traditional face lifting involving the cutting out of skin.

2. Description of Related Art

Cutting (in surgery) will be defined as relatively cleanly breaking through similar or dissimilar tissues with minimal adjacent tissue trauma and thus little tissue stretching, tearing or ripping. Lysis (in surgery) will be defined as breaking through similar or dissimilar tissues with or without adjacent tissue trauma and may involve stretching, tearing or ripping. Depending upon the tissues lysed, the degree of stretching or tearing of lysed tissue edges may be inconsequential or may even result in a desirable benefit such as post surgical contraction. Planes of tissue are not often flat and represent the curviform intersection of dissimilar tissues and are made at least partly of fibrous tissues, either loose and spongy or firm and tough. Planes between the soft internal organs are usually loose and spongy. Planes of tissues in the face and on bones are firm and tough. Undermining will be defined as tissue separation either within or between defined tissue planes. Undermining may be by sharp (instrument) or dull (instrument) depending upon the amount of fibrous tissue binding or existing between the tissue planes to be separated. Undermining is usually performed, as is most surgery, with the intention of minimizing trauma. Sharp instrument undermining is usually performed to separate highly fibrous or collagenous tissues; however, sharp undermining suffers from the risk of penetrating adjacent tissues inadvertently because of loss of ability to follow the desired plane. Inability to follow or maintain the plane in sharp undermining is frequently due to limited visibility, difficulty "feeling" the fibrous plane, or scarring (collagen fibrosis) resulting from previous trauma or surgery. Even experienced surgeons may from time to time lose the correct plane of sharp undermining; great skill is required. Blunt undermining allows a rounded, non-sharp tipped, instrument or even human finger to find the path of least resistance between tissues; once the desired plane is found by the surgeon, it is easy to maintain the plane of blunt undermining until the task is complete. Unfortunately, blunt undermining between highly fibrous tissues such as those that comprise and maintain the shape of the human face usually causes imprecise tunneling with fibrous walls of variable thickness. Dissection usually implies a deliberate and careful sorting out and identification of tissues and usually implies that some sort of undermining has been performed to isolate the desired structure(s). In face-lifting surgery, plastic surgeons have so commonly used the terms undermining and dissection interchangeably that they have become synonymous for the most part in this specific situation. Tracking means to maintain a direction of movement upon forcing a tissue-separating instrument without unpredictable movement or leaving the desired tissue plane(s). Planar tracking means to stay in the same tissue planes. Linear tracking means to move uniformly in a straight or uniformly curved path without unpredictable movement Groups of linear tracks may form a network that creates an undermined tissue plane.

Anatomical Perspective: Lysis or undermining in one dimension (linear=x) implies forming a tunnel. Lysing or undermining in 2 dimensions at any one instant forms a plane (x, y). Traditional face-lift undermining is done just under the leather (dermis) layer of the skin where dermis joins underlying fat or subcutaneous (SQ). Even deeper within the SQ fat run larger blood vessels and delicate, non-regenerating motor nerves to the muscles that give the human face motion and expression. Deep/beneath to the SQ fat reside the muscles and glands of the face. The relevant face-lift anatomy may be referenced in Micheli-Pellegrini V., Surgical Anatomy and Dynamics in Face Lifts, Facial Plastic Surgery 1992:8:1–10, Gosain A. K. et al., Surgical Anatomy of the SMAS: A Reinvestigation, Plast Reconstr Surg. 1993: 92:1254–1263 and Jost G, Lamouche G., SMAS in Rhytidectomy, Aesthetic Plast Surg. 6:69, 1982. The SQ fat differs from body location to body location. On the face, the SQ fat has many fiber-bundles (septae) carrying nerves and blood vessels. If a surgeon were to move, shove, or forwardly-push a blunt, dull-tipped, 1-inch chisel or pencil shaped device through the fat of the face where SQ abuts the dermis, the sheer thickness of the fiber bundles would likely cause slippage of the device and result in the formation of pockets or tunnels surrounded by compacted fiber bundles or septae. Proper performance of a face-lift involves breaking the septae at a proper level to avoid damaging more important structures such as blood vessels and nerves and glands.

Disadvantages of the current techniques are numerous. Face-lifting devices described in the prior art resemble undermining devices that were constructed with cutting edges that rely entirely on the skill of the surgeon to maintain control. Inadvertent lateral cutting or tissue trauma is difficult to control. In addition, speed of separation is affected to ensure accuracy by the surgeon in separating fibrous tissue planes. There are two principle locations for face lift undermining (dissection): in the more common lower facelift (cheek/neck-lift) undermining in the subcutaneous tissues is customarily performed; in the less common upper facelift (which approximates brow-lifting) undermining in the subgaleal or temporalis fascia plane is customarily performed. Use of prior art undermining devices (including scissors, sharp rhytisectors, etc) in these planes during cosmetic surgery has, at times, resulted in unwanted cutting, trauma or perforation of adjacent structures. Scissors and rhytisectors are planar cutting instruments; thus, the position of the cutting edges with respect to the surface of the face is controllable only by the surgeon estimating location, as no $3^{rd}$ dimensional bulbous limitation exists. Unfortunately, scissors with 3 dimensionally "bulbous", rounded tips cannot close all the way to cut target tissue. Scissors with 2 dimensionally rounded tips can close all the way to cut target tissue but may wander inadvertently between tissue planes due to the thin third dimension (thickness) of the scissors blades.

Rubin (U.S. Pat. No. 3,667,470) describes a bone shaver and grooving device that consists of a single sharp edged extension protruding perpendicular to the plane of motion of the cutting edge of the device. The extension is intended to carve and maintain a groove in rigid, immobile, bone as it is driven forward by a surgeon's hammer. This device is impractical for lysing facial planes because the extension would severely damage blood vessels and delicate nerves. In addition, Rubin's invention would not maintain a planar track in soft tissues. Hendel (U.S. Pat. No. 4,600,005) describes a guided osteotome for harvesting cranial bone graft that has a single cutting tip between two bulb like guides at the edges. The guides prevent the hammer driven cutting edge from penetrating the skull too deeply as the harvesting cutting edge would tend to "dive" deep into the skull toward brain tissue if unhindered (vertical tracking control). However, these single guides with their geometry cannot effectively compress or pass through the collagenous, fibrous tissues into recessions making for a more precise lysis of the grouped fibers and bundles.

Current face-lifting instruments that cut with other than manual energy do not address the novel concept of a "protected plane" during energized face-lifting dissection. Current lasers must be fired from positions outside the patient to energize tissue within the face to cut in a very imprecise fashion (See "Manual of Tumescent Liposculpture and Laser Cosmetic Surgery" by Cook R C and Cook K K, Lippincott, Williams, and Wilkins, Philadelphia ISBN: 0-7817-1987-9, 1999). Tissue is damaged with little control. Current electro-surgical devices for face-lift tissue energizing must be delivered through large open pockets or through the limited access and slow moving, tedious endoscopes. Farin (U.S. Pat. No. 5,776,092) describes a single tube device that can deliver laser, ultrasound or radio frequency devices to treat tissue. However, Farin's device is not intended for separating tissue planes and is susceptible to catching, tearing or puncturing the tissue when manipulated. It would be advantageous to provide a safe technique and device for the precise application of energy to properly separate and heat facial tissue while maintaining an exact distance from the delicate surface of the skin. The ideal device achieves this function while minimizing the chances of collateral damage to vital structures such as nerves and delicate vessels. It would be additionally advantageous for the same provisions to allow for a uniform forward tracking and feel of motion of the device that provides a surgeon with instantaneous knowledge. Properly sized and placed protrusions and recessions address all of these problems in a manner not previously possible.

One of the most recent competing procedures to incompletely dissect/lyse/cut a face-lift plane is traditional or ultrasonic liposuction. Unfortunately, dissection is incomplete as the cannulas only make tunnels. The tissues between the tunnels must be cut with scissors in order to create a plane. When the scissors cuts the fiber tissues and blood vessels constituting the walls of the tunnels, bleeding and trauma occur and frequently require spot coagulation under visualization. Other severe drawbacks of the incomplete undermining that liposuction cannulas perform include the common trauma and resultant mouth droop paralysis that occurs in the hands of even prominent surgeons when the delicate and anatomically unpredictable (20% of the population) marginal mandibular branch of the facial nerve is cut. Additionally, ultrasonic cannulas become hot and can cause thermal burns called "end hits" when the cannula tip is thrust against the inside of the skin as is common during the procedure.

Just as sharp undermining or dissection has its disadvantages, as previously mentioned, blunt dissection suffers from its own difficulties as well. Forcing a blunt object through tissue avoids indiscriminate sharp cutting of important structures (nerves, vessels). Blunt undermining compacts the stronger, firmer, strands of collagen even contained within tissues as soft fat into thicker "bands" (some overly thick for uniform cutting). Undesirably for a face lift, traditional blunt object undermining may indiscriminately force aside and compact septae causing incomplete lysis or freeing of the tissues. Also unfortunately for face lifting, traditional purely blunt object undermining will result in random motion or uncontrollable-slippage of the underminer tip on forward motion and thusly loss of precise tracking of the underminer through target tissue.

Currently it takes surgeons between 20 minutes and one hour to carefully and properly dissect/undermine/lyse/lift a lower face. It usually takes between 10 minutes and 30 minutes, depending upon the patient to carefully and properly spot coagulate/seal all of the blood vessels that were cut during the aforementioned lysing portion of the face-lift For upper face lifting, times are less than half that mentioned for lower face lifting. The present invention would reduce time for a surgeon to do both the duties of lysing and coagulation since the device performs both tasks as well as aids in maintaining proper positioning and tracking. The time reduction should be at least 50–75%. Reduced operating time means less time a wound is open to potential infection, lowered surgical costs and less time and therefore less risk under anesthesia and thus a general improvement in the procedure.

There exists a special subset of the general population that may benefit uniquely from the present invention. Men and women between the ages of 35 and 55 are just beginning to droop and develop folds. However, there is not as much undulating wrinkling as in older patients. Currently long incisions of 10–20 cm are made around each of the two ears, for the purposes of hiding the scars. Skin is cut out and discarded and the remaining skin stretched. Unfortunately, skin does not thicken in response to stretching; it only thins. Unfortunately, some plastic surgeons in the early 1990's advocated "prophylactic" or "preemptive" face-lifting on women in their 40's purportedly to "stay ahead of nature." This philosophy has now been discounted and discredited by the vast majority of reputable experts. With the present invention, tightening will be most dramatic in younger patients between 35 and 55 years of age such that surgeons may not have to cut out or stretch skin for a desirable effect for most patients in this population. In this case, the present invention is inserted through only 3 relatively small incisions of less than 1 cm each and energy is applied to the upper subcutaneous, lower dermal and platysmal face-lift layers. If the 3 small incisions can be used and no skin excised, then the procedure will take less than 15 minutes following anesthesia and the effects will last for at least several years.

Given the disadvantages and deficiencies of current face-lifting techiques, a need exists for a device that provides a fast and safe alternative.

SUMMARY OF THE INVENTION

An object of the present invention is to provide a method and a device that can be used by surgeons to provide quick and accurate face-lifting maneuvers that minimize the amount of affected tissue.

It is another object of the present invention to provide an undermining device that can position lysing surfaces at a proper level for fibrous tissue lysing during a face-lift.

Another object of the invention is to provide quick and accurate face-lifting maneuvers.

Still another object of the invention is to provide a surgical face-lifting device that easily maintains the proper dissection plane.

It is a further object of the invention to provide a surgical face-lifting device that easily maintains the proper dissection plane while lysing and delivers thermal radiation to the internal collagenous tissues of the face to induce skin tightening.

Other objects of the invention will be apparent from the disclosure herein.

Thermal effects to the collagenous (dermal, superficial platysma musculature and other) tissues of the face in the facelift plane can cause cosmetically desirable contraction of the dermal tissues with beneficial tightening of the facial tissues. The present invention combines a unique lysing design with means for providing thermal radiation to efficiently lyse and simultaneously induce the thermal contraction necessary for face lifting. The present invention may be used in hospitals as well as office-based surgery and minimizes pain and risk of injury.

The device is comprised of an undermining shaft with a special tip that can be easily positioned between dissection planes in tissue and then manipulated to separate tissue planes and lyse fibrous tissue. A thermal source and delivering means delivers energy to the distal end of the shaft A temperature sensor monitors the tissue temperature, and control electronics process temperature information to control the thermal radiation for optimum tissue contraction. An optional secondary light source that is visible to the surgeon can be used to help visualize the location of the thermal radiation exit window. Optionally the device can also use ultrasound energy or lower frequency vibrational energy delivered down the shaft to improve tissue lysing.

In one embodiment of the invention, the user sets the desired tissue temperature on an external control unit using a touch pad or other user interface. The shaft of the device is then inserted through a small (~1 cm long) incision and positioned at the desired tissue plane. For lower face lifting the surgeon incises the skin in front of the ears and under the chin. Force is then applied to the shaft of the device by the users hand to separate tissue planes while excluding critical structures (nerves, vessels) thus avoiding entanglement or trauma or indiscriminate cutting of these important structures. The same protrusions that exclude critical structures by virtue of their relationship to the recessed cutting segments also serve to position the depth of the present invention with respect to the lower dermis. The spacing of the protrusions (bulbs) and recessions (lysing segments) maintains the tracking of the instrument Tracking is instantly palpable by the surgeon and requires no monitor to know how the device is moving. Both the number and spacing of protrusions in the present invention reduce wobble or lateral (horizontal) slippage during forward thrusting of the shaft. Uniquely, vertical slippage is prohibited as well. The width of the protrusions/bulbs maintains the correct distance between the lysing segments and the delicate underside of the superficial skin or dermis. The tip of the device and the action of the device can be felt/appreciated without direct visualization (endoscope). The surgeon can palpably feet the device is tracking in the proper location. The feel of the device as it moves with palpable and easily grade-able resistance through the facial tissues can immediately tell the user-surgeon the location and the amount of undermining that has occurred at that location.

The unique tip is comprised of alternating, preferably relatively symmetrical-across-a-midline, protrusions and recessions. The protrusions can be bulbous, geometric, etc., as long as the tips of the protrusions are able to push and compress tissues into the cutting recessed segments. The recessed segments have a sharpened edge that effectively lyses the tissue that comes into contact as the device is pushed forward. The close spacing of the grooves (caused by the alternation of tip protrusions and recessions) provides the user with a feel during forced tissue movement and significantly limits slippage. Again, the tip of the device, and the action of the device can be felt/appreciated without direct visualization (endoscope).

If desired by the user, thermal radiation exits an optical window near the distal end of the shaft to heat the tissue that lies near the window. The thermal radiation propagates away from the face to effectively heat the skin layer from the inside out The purpose of the thermal energy is to alter/irritate the collagen so as to controllably cause later shrinkage and optionally to control any bleeding. The power required to coagulate such a layer of tissue is only a few watts. This flux can be provided by a thermal source such as a hot tungsten filament with temperature of about 1000 degrees. Since most preferred thermal sources are not highly visible to the human eye, the device will offer the user the option to simultaneously transmit visible light down the shaft to give the user the ability to visualize the region being treated. For example, red light that is easily transmitted through several millimeters of skin could be safely used to guide the surgeon. Thermal radiation can be controlled manually by the user or alternatively automatically controlled to prevent excessive or inappropriate thermal damage.

An alternative embodiment of the device uses a heated segment near the distal tip of the device to heat the tissue directly. The heated segment could be a thin film resistor that is heated by flowing a current through the film. The temperature of this film would be selected by the user and will typically be less than 80° C. This embodiment eliminates the possibility of the tissue being heated above the desired temperature. In addition, the heated segment can be larger than the thermal radiation output window in previous embodiments without significant risks.

In one embodiment, the temperature of the target tissue is measured with a non-contact temperature sensor and the value displayed and used by the thermal radiation control unit to actively control the thermal radiation. The preferred temperature sensor would be an infrared temperature sensor, but other conventional sensors may be used, such as fiber optic fluorescence temperature sensors, thermal resistance sensors, and thermocouple sensors. In order to improve lysing efficiency, one embodiment of the device incorporates an ultrasound transducer into the hand piece that transmits ultrasound energy down the shaft A lower frequency vibrating transducer could also be incorporated into the device to improve lysing.

In another embodiment, the recessed cutting segments of the device are driven by an electro-surgical RF generator to improve lysing and allow RF heating of tissue.

The present invention can be used to improve the efficacy and safety of face lifting and is thus useful in a variety of cosmetic procedures. The forgoing and other objects, features, and advantages of the present invention will become apparent from the following description and accompanying drawings.

The disclosures of this publication and the disclosures of all other publications recited herein are incorporated by reference as if fully set forth herein. Co-pending U.S. patent applications Ser. Nos. 09/478,172 and 09/475,635 are incorporated herein by reference.

BRIEF DESCRIPTION OF THE DRAWINGS

The accompanying drawings, which are incorporated into and form part of this disclosure, illustrate embodiments of the invention and together with the description, serve to explain the principles of the invention.

FIG. 2 shows a side view of face-lift apparatus attached to articulating arm or fiber optics.

FIG. 3 shows top view of face-lift apparatus attached to articulating arm or fiber optics.

FIG. 4 shows off-center frontal view of tip of face-lift apparatus protrusions and recessions.

DETAILED DESCRIPTION OF THE INVENTION

The present invention provides a device that can be used by surgeons to provide quick and accurate face-lifting maneuvers that minimize the amount of tissue that has to be removed. The device is comprised of an undermining shaft that can be easily positioned between dissection planes in tissue and then manipulated to separate tissue planes and lyse fibrous tissue, a means for heating tissue near the distal end of the shaft, a temperature sensor that monitors the tissue temperature, and control electronics that process temperature information to control the thermal radiation for optimum tissue contraction. An optional secondary light source that is visible to the surgeon can be used to help visualize the location of the thermal radiation exit window. Optionally, the device can also use ultrasound energy delivered down the shaft to improve tissue lysing.

Figure 1:
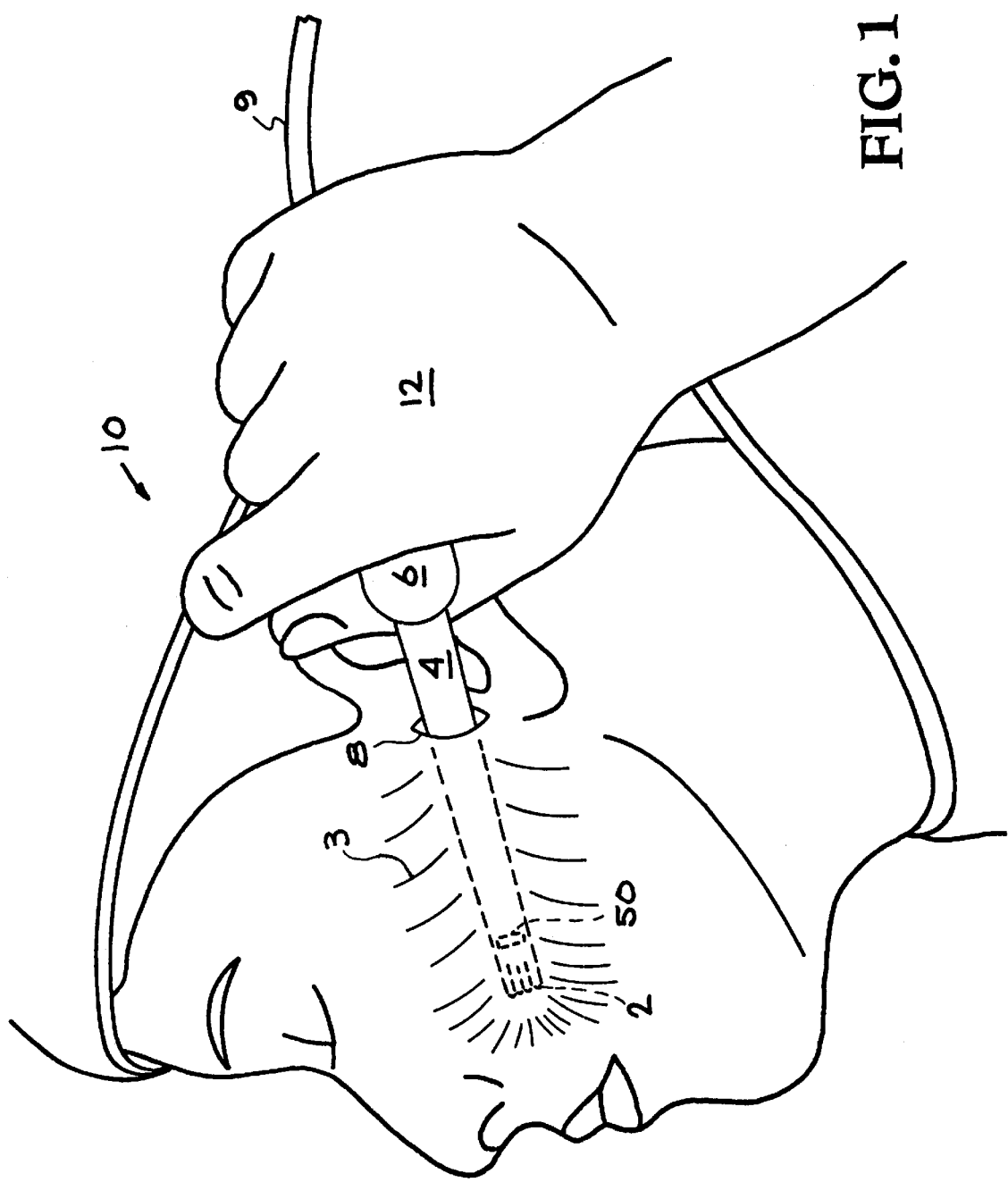
FIG. 1 shows present invention (and partial top view of face lift apparatus) in use.

FIG. 1 shows a partial top view of an embodiment of the face-lift apparatus 10 of the present invention as it is being used. The handle 6 is gripped in the hand 12 of the user of the device. The shaft 4 with the special lysing tip 2 is inserted through an opening 8 at a suitable location on the face of a patient. Dashed lines indicate the portion of the device hidden from view under the skin. Curved stretch lines 3 indicate the upward force applied on the device 10 and therefore shaft 4 and the overlying skin of the face. The apparatus may then be thrust forwardly while lifted forcefully by the operator to perform its function and maintain the plane of undermining. Window 50 (dashed and hidden from clear view in this representation) allows thermal radiation to escape from within the shaft 4.

FIG. 2 is a side view of the face-lift apparatus 10. The tip 2 may be slightly larger than the shaft 4. The tip 2 can be a separate piece that is secured to shaft 4 by a variety of methods such as a snap mechanism, mating grooves, plastic sonic welding, etc. Alternatively, in this model tip 2 can be integral or a continuation of shaft 4 made of similar metal or materials. The tip 2 may also be constructed of materials that are both electrically non-conductive and of low thermal conductivity; such materials might be porcelain, ceramics or plastics. Portions of the tip and shaft may be covered with Teflon to facilitate smooth movement of the device under the skin. An optional electrically conductive element 61 may be provided to bring RF electro surgical energy to metal or electrically conductive elements mounted in the recessions (see FIG. 3). The shaft 4 is tubular in shape or can be a somewhat flattened tube oblong in cross section. The shaft 4 is made of metal with a hollow interior that can contain insulated wire or wires 61. Alternatively, the shaft 4 may the made of plastic that will act as its own insulation about wire or electrically conductive element 61. The optional electrically conductive element 61 internal to shaft 4 conducts electrical impulses or RF signals from an optional external power/control unit (such as a Valleylab Surgistat, Boulder, Colorado). An optional temperature sensor 35 placed near the distal tip of the shaft is used to monitor the local temperature. This information can be used by the control electronics to control the energy delivered to the tip. An ultrasound transducer 32 can also be activated to transmit energy to the tip 2 and provide additional heating and improve lysing.

FIG. 3 is an enlarged plan or top view of the tip 2 as used in upper face-lift This tip 2 shows four protrusions 26 and three recessions 28. The groove created by the tapering recessions may be up to one centimeter in length. The width of this tip varies between 12 mm to 20 mm and the thickness varies between 3 mm to 4 mm. Optical window 50 allows thermal radiation to exit the shaft and irradiate tissue directly above the window. The user can enable or disable the thermal source through a hand or foot switch (not shown).

Figure 5:
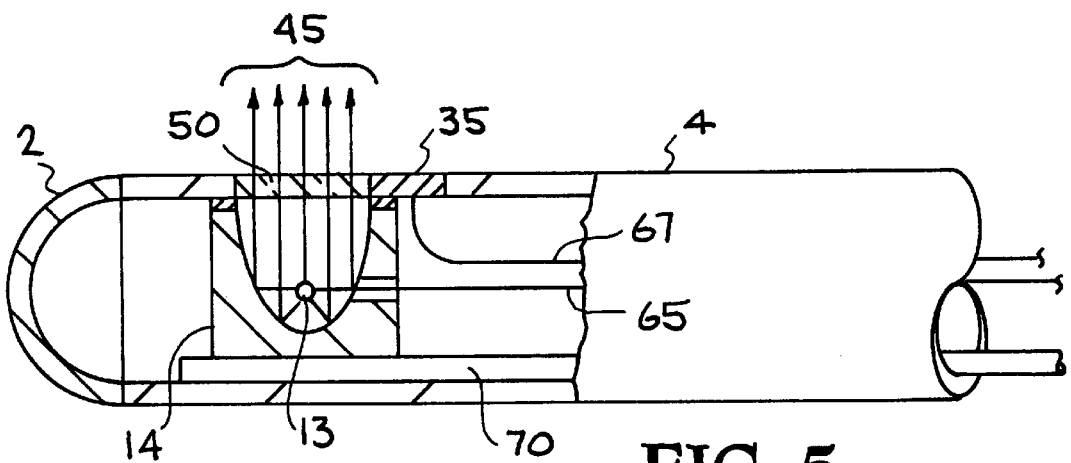
FIG. 5 shows a cross-sectional view of the distal tip showing a compact thermal source for heating tissue.

FIG. 4 shows an off-center frontal view of the tip of the face-lift apparatus protrusions and recessions. The tip 2 has four protrusions 26 and three recessions 28 in which are seated electrodes 81. The RF electrodes 81 located at the most proximal portion of the cutting recessions can increase lysing and coagulation at the cutting edge. The RF electrodes 81 are connected by conducting wires 61 (FIG. 2) to the power/control unit The user can enable or disable the RF power through a hand or foot switch (not shown). Window 50, allowing egress of thermal radiation and temperature sensor 35 are also located on the tip and may be of varying sizes. The width of this tip varies between 5 mm and 10 mm while the thickness may vary between 2 mm to 4 mm. The tip, however, is not constrained by those dimensions. FIG. 5 shows a cross sectional view of an embodiment of the face-lift device 10 of the present invention. The shaft 4 with the special lysing tip 2 is inserted through an opening at a suitable location on the face of a patient. The apparatus may then be thrust forwardly while lifted forcefully by the operator to perform its function and maintain the plane of undermining. A hot filament 13 within the device is heated by flowing current through connecting wires 65. The filament 13 is held rigidly in position within the parabolic cavity by the strength of the wire 56. Alternately, the filament 13 is fixedly attached to the shaft 4. The hot filament 13 emits optical and thermal radiation 45 that can directly exit window 50 or be reflected off a reflector 14 to also exit through window 50. The reflector 14 can have a parabolic shape to effectively collect all optical and thermal radiation emitted away from the window 50. The hot filament 13 can be a tungsten carbide filament similar to those used in high power light bulbs. The wavelength may be adjusted and controlled by adjusting the filament temperature/current The window 50 can be selected from a wide variety of glass that transmits optical, near infrared and infrared light (e.g. quartz, fused silica and germanium.) The tissue penetration depth depends on the wavelength of the light (e.g., 1 $\mu$m penetrates through 10 mm, 10 $\mu$m penetrates through 0.02 mm). The broad emission spectrum from the hot filament 13 can be filtered by window 50 to achieve the desired tissue effect In particular filtering the emission spectrum to heat the dermis to temperatures of approximately 70° C. will cause the desired collagen shrinkage and tightening. The optimum spectral filtering depends on skin thickness and structure. A temperature sensor 35 connected to the control unit by electrical wire 67 monitors the temperature of tissue that is in contact with the shaft 4. In order to eliminate excessive heating of the shaft 4 and the surrounding facial tissue, the heating element 13 and reflector 14 are thermally isolated by low thermal conductivity materials. The heating element is isolated by not touching the shaft, whereas the reflector can have an isolating layer where it attaches to the shaft In addition, cold nitrogen gas can be injected through tube 70 and pumped out through the hollow shaft to cool the tip 2 and shaft 4. Flowing nitrogen gas through the hollow shaft also reduces oxidation damage to the filament.

Figure 6:
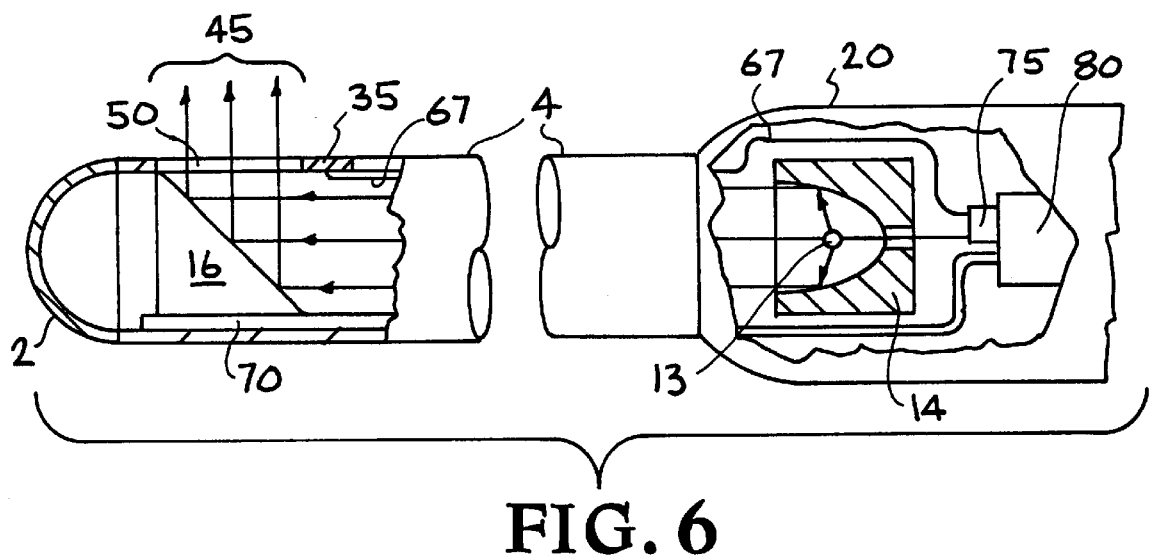
FIG. 6 shows a cross-sectional view of an alternative embodiment of the present invention that contains the thermal source in the handpiece.

FIG. 6 shows an alternative embodiment of the present invention that reduces the thermal load to the shaft 4 and eliminates the need for high electrical currents within the shaft. In this embodiment the hot filament 13 is located in the handle 20 of the device and is connected to the power unit by wires 65 and cable 75. The optical and thermal radiation 45 is transported through the hollow wave-guide within the shaft 4 and reflected off the mirror 16 through the window 50. The absorption coefficient within the wave-guide is inversely proportional to the cube of the height of the hollow wave-guide within the shaft and can be made small for the hot filament 13 when operated at temperatures greater than 600 degrees. The absorbed energy would be evenly distributed over the entire shaft 4 and the average temperature increase would be small. A mirror reflector 14 redirects radiation emitted away from the shaft down the shaft to improve overall system efficiency. A temperature sensor 35 connected to the control unit by electrical wire 67 and cable 75 monitors the temperature of tissue that is in contact with the shaft 4. The ability to continuously monitor the temperature greatly reduces the danger of overheating and tissue carbonization. In addition, cold nitrogen gas can be injected through tube 70 to cool the tip 2 and shaft 4. The nitrogen gas can exit through the handle 20 or be recirculated through a cooling system. Flowing nitrogen gas through the hollow shaft also reduces oxidation damage to the filament. A cable 80 connects the present device to the control/power unit.

Figure 7:
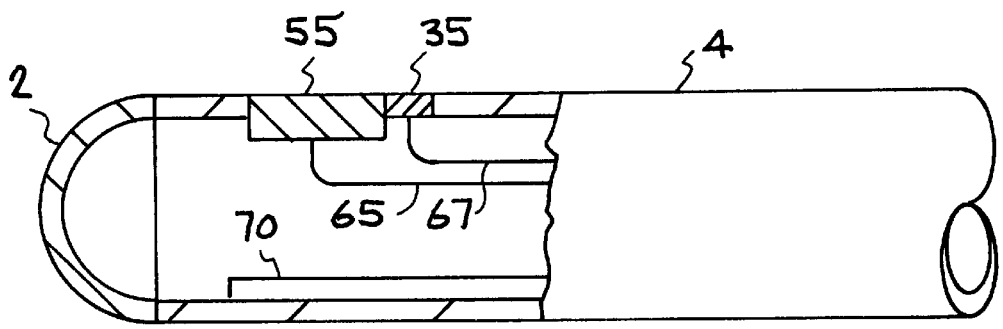
FIG. 7 shows a cross-sectional view of face-lift apparatus that uses a hot surface to heat tissue.

FIG. 7 shows an alternative embodiment of the present invention in which tissue heating is achieved by the direct contact with a hot surface 55. In this embodiment electric current flowing through wires 65 heat a resistive load 55 to a user selected temperature. For most applications the temperature will be less than 80° C. to induce collagen shrinkage but prevent thermal collateral damage. This embodiment eliminates the risk that any tissue region can be heated above the desired temperature by misuse. This allows the size of the hot surface 55 to be larger (e.g. several centimeters long, 1 centimeter wide) which can speed up the procedure. In addition the hot surface 55 can be made up of multiple elements that can be set to different desired temperatures. The resistive load could be a thin film resistor and the film temperature could be estimated from the measured resistance. Alternatively a separate temperature sensor 35 can be placed close to the heating element The measured temperature is used by the control unit to control the current through the resistive load. In order to reduce heating to the shaft 4 and tip 2, cold gas or liquid can be injected through tube 70 and pumped out through the hollow shaft The specific shape of the heater 55 and surface temperature can be adjusted to obtain the desired tissue coagulation depth. Instead of a resistive load, the heating element could be the hot side of a Peltier thermoelectric cooler. An advantage of a thermoelectric cooler is that the opposite surface is cooled below ambient temperature. Single stage thermoelectric coolers can achieve temperature differences of up to 40° C. By thermally connecting the cold surface of the thermoelectric cooler to the bottom of the shaft the cooler can be used to reduce heating of the shaft away from the hot surface.

In all embodiments of the device the shaft can be coated with a biocompatible non-stick material such as Teflon® to reduce tissue sticking to the device during the procedure.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

What is claimed is:

1. An apparatus for separating tissue planes and providing thermal radiation to tissue, comprising:
    a shaft having a proximal end and a distal end;
    a plurality of protruding members on said distal end of said shaft separated by at least one lysing segment that is recessed relative to said protruding members, wherein said lysing segment and said protruding members form a tip having a first cross-sectional area that is less than a second cross-sectional area of said tip that is about perpendicular to said first cross-sectional area, wherein said tip is configured to separate facial tissue substantially in a plane; and
    means connected to said shaft for providing thermal radiation for transmission to targeted tissue.

2. The apparatus of claim 1, wherein said means for providing thermal radiation include an optical window in said shaft, wherein said optical window is operatively positioned for transmitting thermal radiation to said tissue.

3. The apparatus of claim 1, further comprising a temperature sensor fixedly connected to said shaft, wherein said temperature sensor is operatively connected near said distal end of said shaft to monitor tissue temperature.

4. The apparatus of claim 3, further comprising control electronics that process temperature information to control the thermal radiation for optimum tissue contraction.

5. The apparatus of claim 4, further comprising a user interface operatively connected to said control electronics.

6. The apparatus of claim 5, wherein said user interface comprises a touch pad.

7. The apparatus of claim 2, further comprising means for providing visible radiation for transmission through said window to aid in a determination of the location of said window when said window is beneath tissue.

8. The apparatus of claim 1, further comprising an ultrasound transducer within said shaft operatively connected near said distal end for providing ultrasound energy to said tissue.

9. The apparatus of claim 1, wherein said lysing segment comprises a sharpened edge that effectively lyses tissue that comes into contact with said distal end as said apparatus is pushed forward.

10. The apparatus of claim 2, wherein said means for providing thermal radiation comprises a filament.

11. The apparatus of claim 3, wherein said temperature sensor is selected from a group consisting of an infrared temperature sensor, a fiber optic fluorescence temperature sensor, a thermal resistance sensor and a thermocouple sensor.

12. The apparatus of claim 1, wherein said lysing segment comprises means for providing radio frequency energy to improve tissue lysing and provide tissue heating.

13. The apparatus of claim 1, wherein said distal end is attached to said shaft by a mechanism selected from a group consisting of a snap mechanism, mating grooves and a plastic sonic weld.

14. The apparatus of claim 1, wherein said shaft comprises material that is both electrically non-conductive and of low thermal conductivity.

15. The apparatus of claim 14, wherein said shaft comprises material selected from a group consisting of porcelain, ceramic and plastic.

16. The apparatus of claim 1, wherein said shaft is at least partially covered with Teflon® to facilitate smooth movement of said apparatus under skin.

17. The apparatus of claim 10, wherein said filament comprises a tungsten carbide filament.

18. The apparatus of claim 10, further comprising a reflector operatively positioned near said filament to effectively reflect optical and thermal radiation through said optical window.

19. The apparatus of claim 2, wherein said optical window comprises glass selected from a group consisting of quartz, fused silica and germanium.

20. The apparatus of claim 2, wherein said optical window comprises an optical filter.

21. The apparatus of claim 1, further comprising means for controlling the heating of said shaft.

22. The apparatus of claim 21, wherein said means for controlling the heating of said shaft comprises means for thermally isolating from said shaft said means for providing thermal energy.

23. The apparatus of claim 21, wherein said means for controlling the heating of said shaft comprises means for flowing cold nitrogen through said shaft.

24. The apparatus of claim 10, wherein said filament is located near said distal end.

25. The apparatus of claim 10, wherein said means for providing thermal radiation comprises a mirror fixedly and operatively located near said distal end, wherein said filament is located near said proximal end, wherein said shaft comprises a hollow waveguide, wherein thermal and optical radiation from said filament are transported through said hollow wave-guide and reflected off said mirror and through said optical window.

26. The apparatus of claim 25, further comprising a reflector operatively located near said filament to direct radiation emitted away from said distal end toward said mirror.

27. An apparatus for separating tissue planes and providing heat to tissue, comprising:

a shaft having a proximal end and a distal end;

a plurality of protruding members on said distal end of said shaft separated by at least one lysing segment that is recessed relative to said protruding members, wherein said lysing segment and said protruding members form a tip having a first cross-sectional area that is less than a second cross-sectional area of said tip that is about perpendicular to said first cross-sectional area, wherein said tip is configured to separate facial tissue substantially in a plane; and a segment that may be heated located near said distal end of said apparatus and connected to said shaft, wherein said segment can heat tissue directly.

28. The apparatus of claim 27, wherein said segment comprises a thin film resistor, said apparatus further comprising means for flowing a current through said thin film resistor.

29. The apparatus of claim 28, further comprising a temperature sensor placed in proximity to said thin film resistor.

30. The apparatus of claim 27, wherein said segment comprises a Peltier thermoelectric cooler.

31. The apparatus of claim 1, wherein at least one lysing segment comprises a cutting edge.

32. An apparatus for separating tissue planes and providing thermal radiation to tissue, comprising:

a shaft having a proximal end and a distal end;

a plurality of protruding members on said distal end of said shaft separated by at least one lysing segment that is recessed relative to said protruding members, wherein at least one lysing segment comprises a cutting edge; and means connected to said shaft for providing thermal radiation for transmission to targeted tissue.

* * * * *